(12) United States Patent
Jones et al.

(10) Patent No.: US 6,852,980 B2
(45) Date of Patent: Feb. 8, 2005

(54) ON-LINE DOI REBINNING FOR LSO PET/ SPECT SPATIAL RESOLUTION

(75) Inventors: William F. Jones, Knoxville, TN (US); Bernard Bendriem, Knoxville, TN (US); Michael E. Casey, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 274 days.

(21) Appl. No.: 09/982,344

(22) Filed: Oct. 18, 2001

(65) Prior Publication Data

US 2004/0069951 A1 Apr. 15, 2004

Related U.S. Application Data

(60) Provisional application No. 60/241,400, filed on Oct. 18, 2000.

(51) Int. Cl.[7] .................................................. G01T 1/20
(52) U.S. Cl. .............. 250/369; 250/363.02; 250/363.04
(58) Field of Search ....................... 250/363.02, 363.04, 250/366, 369

(56) References Cited

U.S. PATENT DOCUMENTS 6,490,476 B1 * 12/2002 Townsend et al. .......... 600/427

OTHER PUBLICATIONS

S.J. Glick, et al., "the Effect of Photon Incident Angle on Spatial Resolution with Thick Crystal Hybrid PET," The Journal of Nuclear Medicine—Proceedings of the 47th Annual Meeting, Jun. 5, 2000.

* cited by examiner

Primary Examiner—Constantine Hannaher
Assistant Examiner—Timothy J. Moran
(74) Attorney, Agent, or Firm—Pitts & Brittian, P.C.

(57) ABSTRACT

A method and apparatus for on-line DOI rebinning for LSO PET/SPECT to improve spatial resolution, for use in a hybrid Positron Emission Tomography (PET)/Single Photon Emission Computed Tomography (SPECT) system running in PET-mode. Data acquisition hardware is used to feed a detector pair coincidence event stream to an on-line rebinner. Gamma centroid location measurements are made by rastering assumed transaxial and radial head positions and the corresponding rebinning maps for optimal back-projected image resolution. Optimal positions are found by collecting a 64-bit list mode file, assuming a crystal position as the centroid for each of the heads, defining a sequence for varying the assumed positions, making the rebinning look-up tables, rebinning the list mode data, histogramming and reconstructing the image, assessing the image resolution, recording the best resolution number and the associated trial position variables, repeating these on the next trial variable set.

10 Claims, 8 Drawing Sheets

  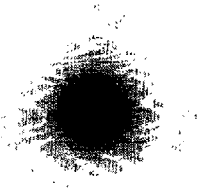
Fig.9A    Fig.9B    Fig.9C
  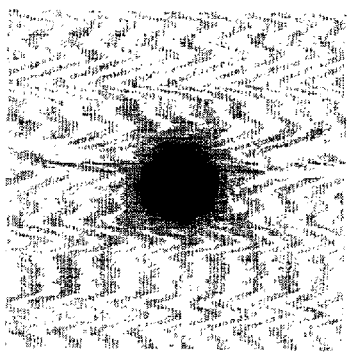
Fig.10A    Fig.10B    Fig.10C

ON-LINE DOI REBINNING FOR LSO PET/SPECT SPATIAL RESOLUTION

CROSS-REFERENCE TO RELATED APPLICATIONS

This application claims the benefit of U.S. Provisional Application No. 60/241,400, filed Oct. 18, 2000.

STATEMENT REGARDING FEDERALLY SPONSORED RESEARCH OR DEVELOPMENT

Not Applicable.

BACKGROUND OF THE INVENTION

1. Field of Invention

This invention relates to the field of tomography devices. More specifically, the present invention relates to a method for using on-line depth-of-interaction (DOI) rebinning in an LSO PET/SPECT system to improve spatial resolution.

2. Description of the Related Art

Detector systems with depth-of-interaction (DOI) capability for 3-D PET have been developed for tomographs by CTI/Siemens, Knoxville, Tenn. Both the HRRT & LSO PET/SPECT tomographs utilize state-of-the-art planar detector designs which feature a high ratio of scintillation crystals to photomultiplier tubes (PMT) permitting many crystals per planar array, effective dual-layer DOI by scintillation decay time, and potentially low manufacturing cost.

BRIEF SUMMARY OF THE INVENTION

The present invention provides a method and apparatus for on-line DOI rebinning for LSO PET/SPECT to improve spatial resolution. The present method is useful in a hybrid Positron Emission Tomography (PET)/Single Photon Emission Computed Tomography (SPECT) system running in PET-mode to improve spatial resolution. The method is especially useful for such a system having a rotating dual-head tomograph using LSO/NaI scintillators and capable of depth-of-interaction (DOI) measurement.

In the preferred embodiment, each detector head in the PET/SPECT system contains two 84×120 planar arrays of crystals, the crystals in the first planar array being fabricated from a first scintillator material and the second planar array being fabricated from a second scintillator material. In PET mode, each head is radially offset 36 cm from the field of view (FOV) center. Relative orientation of the two heads is 158 degrees. Dual-level DOI discriminates between the two scintillator materials by scintillation pulse decay time. While significant for good image resolution, dual-level DOI isolates gamma detection only to the 1 cm long axis depth of each individual crystal. Critical to delivery of excellent spatial resolution are additional methods to precisely characterize the depth of the centroid of the probability of gamma interaction along the long axis of the crystal. The depth is measured to +/−0.01 cm for each of 4 planar arrays and applied for more accurate line of response (LOR) positioning in super-fast real-time rebinding hardware. With DOI and measured centroid depth applied, the full width half maximum (FWHM) transaxial spatial resolution is 0.4 cm at the center of the FOV, and 0.6 cm at 10 cm off center. The DOI discrimination improves resolution as much as fifty percent (50%). More specifically, without DOI discrimination, resolution can degrade by as much as thirty-three percent (33%).

Two rotating detector heads for use in PET mode are supported by a gantry. A movable patient bed is provided for introducing the patient into and removing the patient from within the patient gantry. Two planar detector arrays are served by an array of PMT's. The dual layer planar detector head is comprised of a PMT array, a light guide, and the two layers of crystals in a light-tight container. The light guide is disposed below the two layers of crystals and above the PMT array.

The data acquisition hardware includes a TAXI to Fibre Channel Adaptor card, or TFA, and a rebinner. The TFA feeds the detector pair coincidence event stream to the rebinner for on-line rebinning. The bin address output stream from the rebinner feeds a Fibre Channel PCI DMA receiver card for direct PCI DMA stream transfers controlled by the computer system operator software. The stream is useful for storage on disk or for on-line histogramming directly into PC DRAM. Each of these components is carried on and in electrical communication with an embedded PC motherboard. The rebinner circuit supports on-line real-time DOI LOR-to-projection-space nearest-neighbor rebinning. All DOI and gamma interaction centroid depth knowledge about LOR positioning is applied in real time.

Gamma centroid location measurements to ±0.01 cm are made by rastering assumed transaxial and radial head positions and the corresponding rebinning maps for optimal back-projected image resolution. Four variables are used to define position rasterization. These variables represent the radial and transaxial offsets, or centroid positions, for each of the heads. During rasterization, the four variables are each stepped discretely through a chosen range, with all combinations of the parameters being tested.

The optimal positions, and thus the centroid locations, are found using the following process. A 64-bit list mode file is collected once and read a multiple of times. The process is initiated by assuming a crystal position as the centroid for each of the heads. A sequence for varying the assumed positions is also defined at the outset. First, the indicated rebinning look up tables are made. Next, the list mode data is rebinned. The image is then histogrammed and reconstructed. Following this step, the image resolution is assessed. Next, the best resolution number and the associated trial position variables are recorded. These steps are then repeated on the next trial variable set. All FWHM resolution numbers are assessed from a conventional 2-D filtered back projection of the sinogram using a ramp filter with a 0.5 cutoff. In all applications, both image horizontal and vertical FWHM assessments are performed. Only the higher of the two FWHM is used for making decisions.

Initially, the four centroid locations are found using only LSO-LSO coincidence data. The sequence involves the rasterization of the four variables compensated not only for detector physics but also for simple mechanical variation in the mounting of the detectors. Once the centroid positions for the LSO crystals are known, a simpler problem remains for finding the NaI centroid locations. The NaI transaxial locations are assumed to be equivalent to the LSO case. Only the NaI radial locations remain to be determined. This determination requires a step-sequence with only one variable as opposed to four. Only LSO-NaI coincidence data is used for finding this fifth radial offset position. During rasterization, the position variable is allowed to affect only the NaI end of each LOR. The LSO end of each LOR use the four LSO-only position parameters as determined and fixed earlier.

To this point, rasterization has been performed on data collected with the needle source positioned very close to the FOV center. Once these five position parameters (four for LSO crystals and one for NaI crystals) are determined, the final rebinning look-up table is defined. This look-up table is then applied for general use, including for LOR which do not serve the FOV center.

BRIEF DESCRIPTION OF THE SEVERAL VIEWS OF THE DRAWINGS

The above mentioned features of the invention will become more clearly understood from the following detailed description of the invention read together with the drawings in which:

FIGS. 9A–9C display the sinograms and optimized images from the on-line center needle data collection;

FIGS. 10A–C illustrate the sinograms and images from the off-center needle data collection, the offset being 10 cm.

DETAILED DESCRIPTION OF THE INVENTION

A method and apparatus for on-line DOI rebinning for LSO PET/SPECT to improve spatial resolution incorporating various features of the present invention is illustrated in the figures. The present method is useful in a hybrid Positron Emission Tomography (PET)/Single Photon Emission Computed Tomography (SPECT) system running in PET-mode to improve spatial resolution. The method is especially useful for such a system having a rotating dual-head tomograph using LSO/NaI scintillators and capable of depth-of-interaction (DOI) measurement.

In the preferred embodiment, each detector head in the PET/SPECT system contains two 84×120 planar arrays of crystals. The crystals in the first array are fabricated from NaI. The crystals in the second array are fabricated from LSO. In one embodiment, each of the LSO and NaI crystals are 0.44 cm×0.44 cm×1 cm.

In PET mode, each head is radially offset 36 cm from the field of view (FOV) center. Relative orientation of the two heads is 158 degrees. Dual-level DOI discriminates LSO versus NaI by scintillation pulse decay time. While significant for good image resolution, dual-level DOI isolates gamma detection only to the 1 cm long axis depth of each individual crystal. Critical to delivery of excellent spatial resolution are additional methods to precisely characterize the depth of the centroid of the probability of gamma interaction along the long axis of the crystal. The depth is measured to +/−0.01 cm for each of 4 planar arrays and applied for more accurate line of response (LOR) positioning in super-fast real-time rebinding hardware. With DOI and measured centroid depth applied, the full width half maximum (FWHM) transaxial spatial resolution is 0.4 cm at the center of the FOV, and 0.6 cm at 10 cm off center. The DOI discrimination improves resolution as much as fifty percent (50%). More specifically, without DOI discrimination, resolution can degrade by as much as thirty-three percent (33%).

Figure 1:
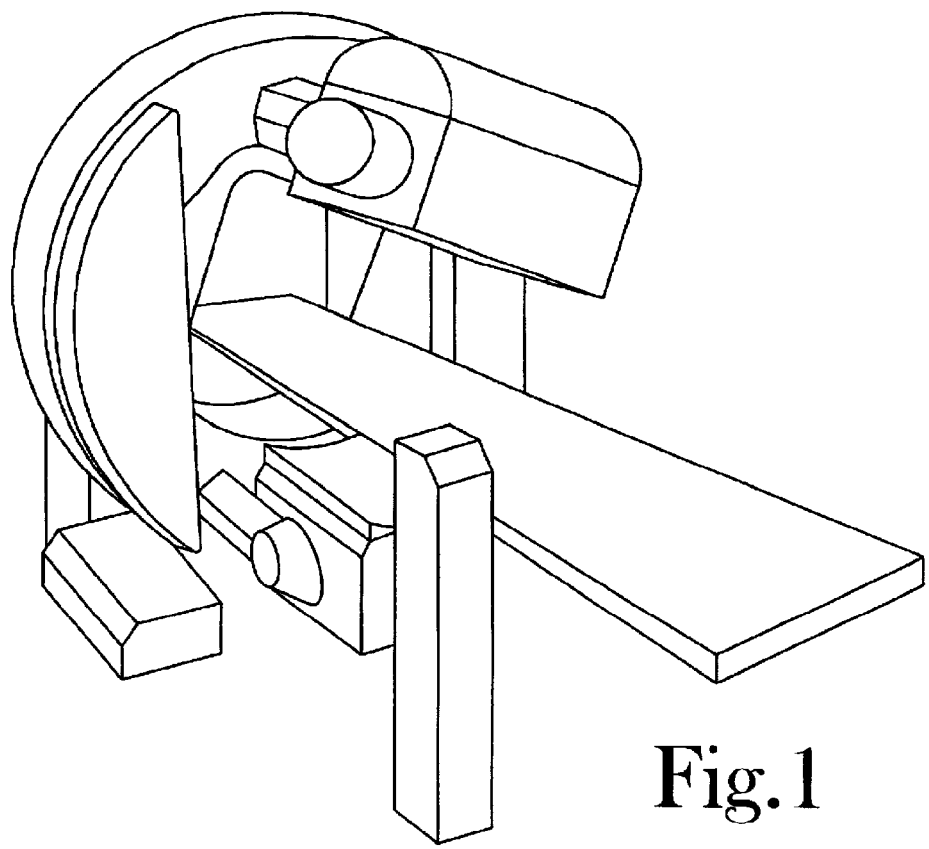
FIG. 1 illustrates an LSO PET/SPECT device.

FIG. 1 illustrates an LSO PET/SPECT device. Two rotating detector heads for use in PET mode are supported by a gantry. A movable patient bed is provided for introducing the patient into and removing the patient from within the patient gantry. Two planar NaI/LSO detector arrays are served by an array of PMT'S, one array being comprised of NaI detectors and the other LSO detectors. Each detector array is comprised of 84×120 detectors. The PMT array is comprised of 8×11 PMT's. The resulting cylindrical FOV within the gantry has a 55 cm diameter and is 37 cm long.

Figure 2:
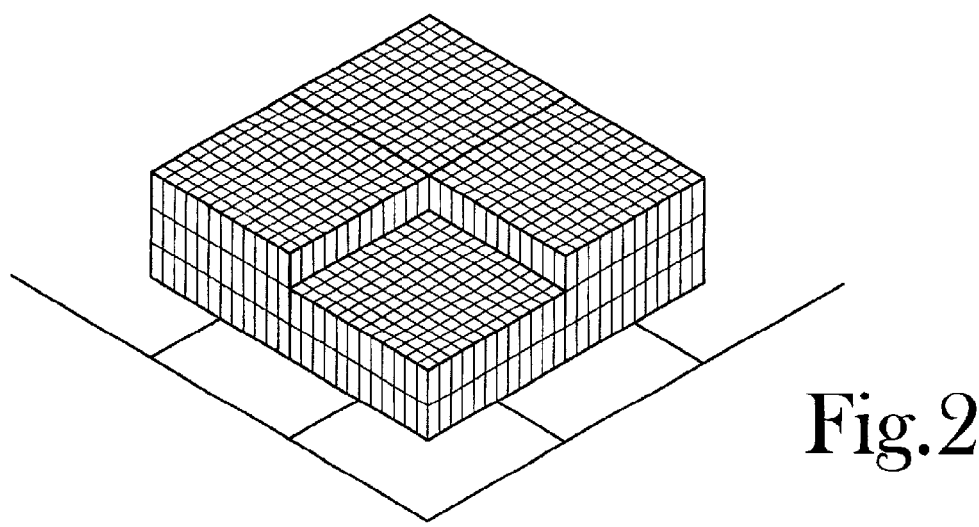
FIG. 2 illustrates an enlarged cut-away view of the dual layer planar detector head used in the LSO PET/SPECT device of FIG. 1.

FIG. 2 illustrates an enlarged cut-away view of the dual layer planar detector head. Illustrated are the PMT array, a light guide, and the two layers of crystals in a light-tight container. The upper most planar detector array, closest to the center of the FOV, is comprised of NaI crystals. The next lower planar detector array is comprised of LSO crystals. Each of the LSO and NaI crystals are 0.44×0.44×1 cm. The light guide is disposed below the LSO detector array. In the preferred embodiment the light guide is fabricated from plastic. The PMT array is disposed below the light guide.

Figure 3:
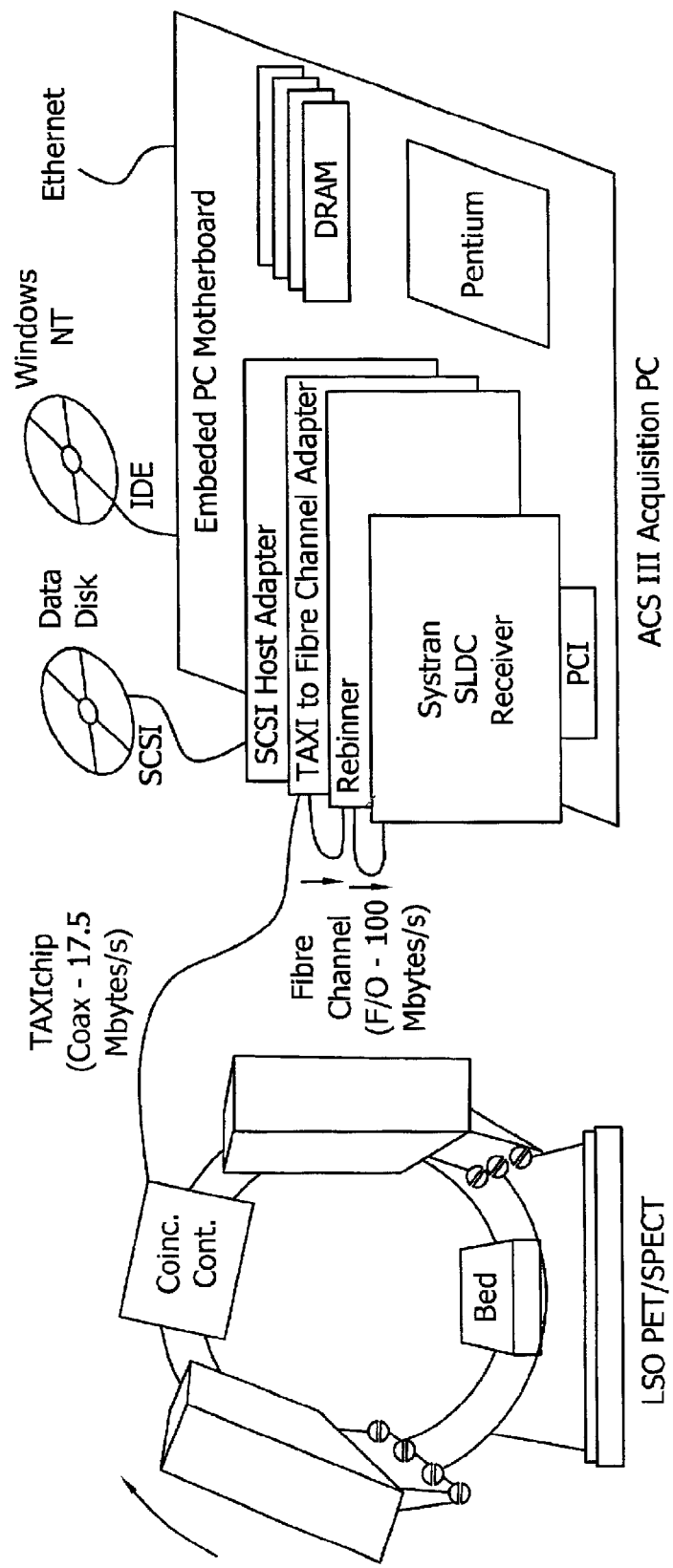
FIG. 3 illustrates one embodiment of the data acquisition hardware used in the method of the present invention.

FIG. 3 illustrates one embodiment of the data acquisition hardware. In the data acquisition hardware of the preferred embodiment for use with PET/SPECT with LSO scintillators, the PET coincidence stream is processed successively through two custom PC cards. Of course, it will be understood that other alternative architecture may be used as well. The two cards depicted include a TAXI to Fibre Channel Adaptor card, or TFA, and a rebinner. The TFA feeds the detector pair coincidence event stream to the rebinner for on-line rebinning. The bin address output stream from the rebinner feeds a Fibre Channel PCI DMA receiver card for direct PCI DMA stream transfers controlled by the computer system operator software. The stream is useful for storage on disk or for on-line histogramming directly into PC DRAM. Each of these components is carried on and in electrical communication with an embedded PC motherboard.

Figure 4:
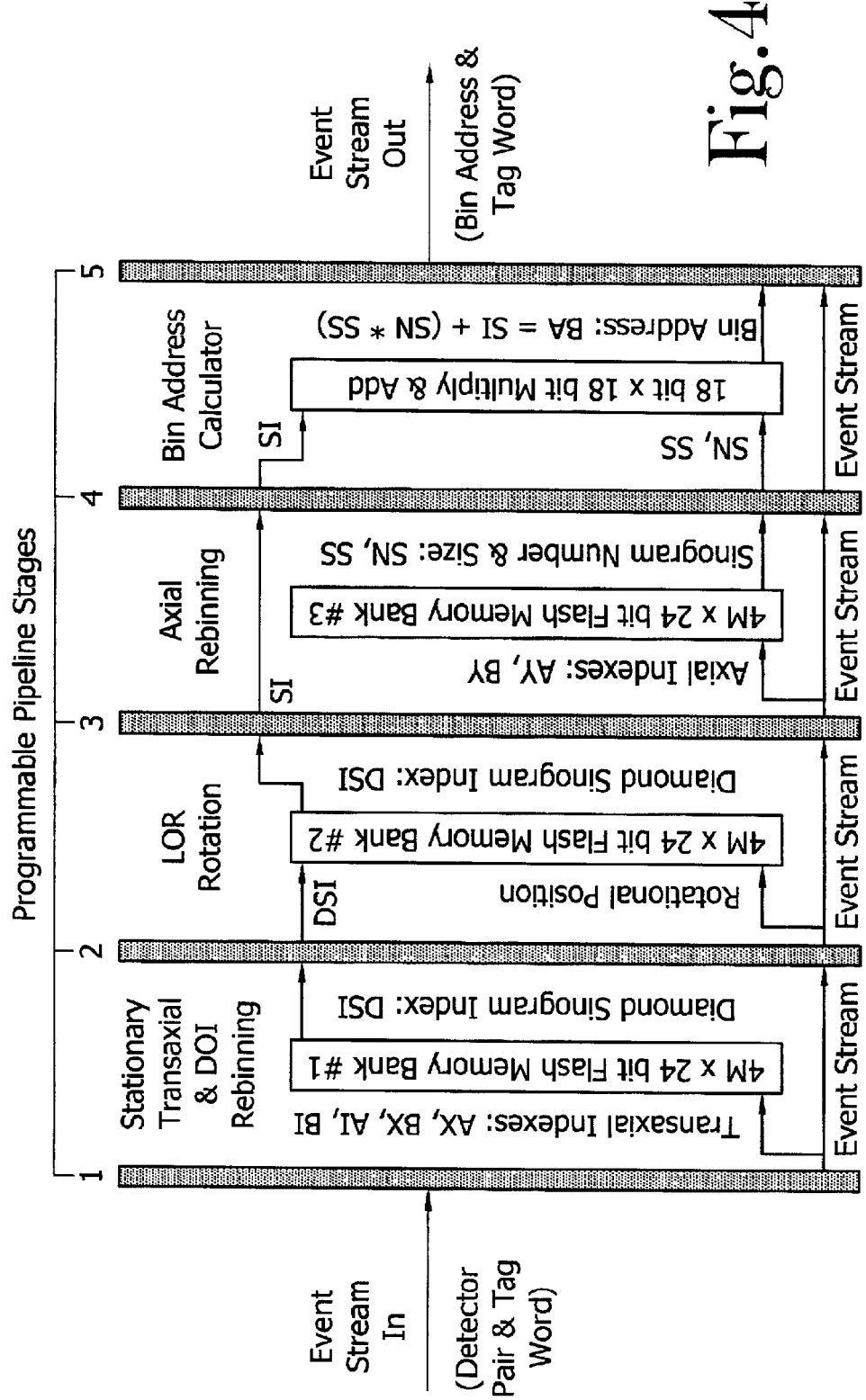
FIG. 4 illustrates a block diagram of the rebinner circuit incorporated in the data acquisition hardware illustrated in FIG. 3.

FIG. 4 illustrates a block diagram of the rebinner circuit, which supports on-line real-time DOI LOR-to-projection-space nearest-neighbor rebinning. All DOI and gamma interaction centroid depth knowledge about LOR positioning is applied in real time by this design.

Figure 5:
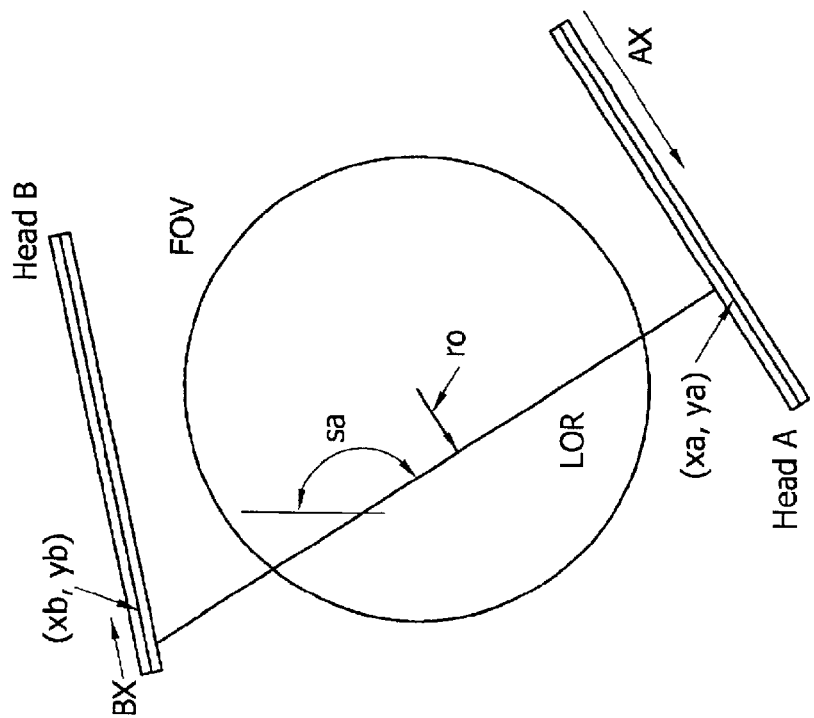
FIG. 5 illustrates a portion of the transaxial computation performed by one bank of the rebinner.

Illustrated in FIG. 5 is a portion of the transaxial computation performed by one bank of the rebinner. A transaxial slice view of the PET/SPECT FOV with the detectors from heads A and B is shown, with the detector event occurring along a line between one detector $(x_A, y_A)$ in head A and another detector $(x_B, y_B)$ in head B. The sinogram angle sa is determined by the equation:

$$sa = \tan^{-1}\left[\frac{y_b - y_a}{x_b - x_a}\right], \quad (1)$$

and where the radial offset ro is determined by the equation:

$$ro = \sqrt{(x_a^2 + y_a^2)} \cdot \sin(\tan^{-1}(y_a/x_a) - sa) \quad (2)$$

Figure 6:
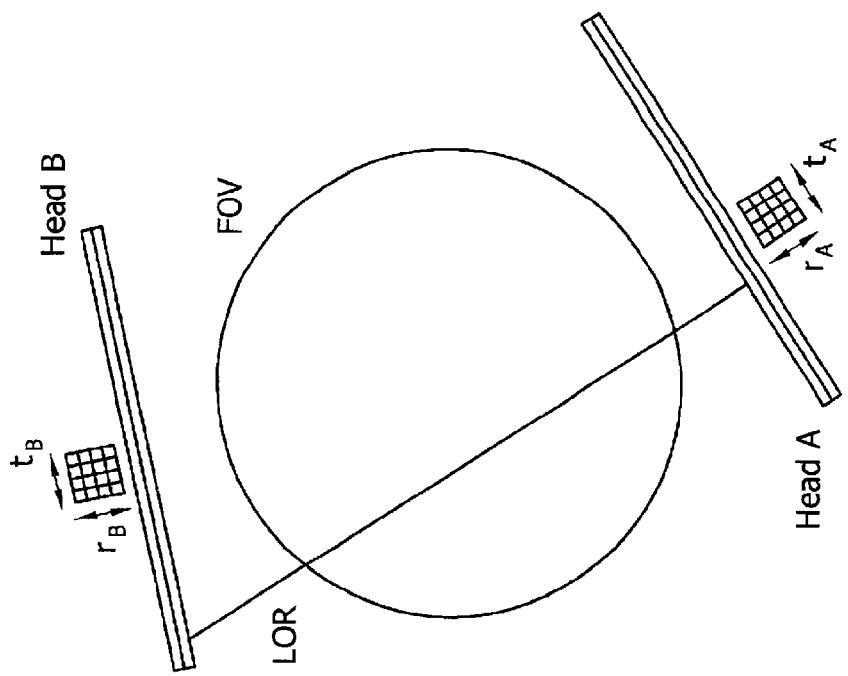
FIG. 6 illustrates the four variables $r_A$, $t_A$, $r_B$, $t_B$ used to define position rasterization.

Gamma centroid location measurements to ±0.01 cm are made by rastering assumed transaxial and radial head positions and the corresponding rebinning maps for optimal back-projected image resolution. FIG. 6 illustrates the four variables $r_A$, $t_A$, $r_B$, $t_B$ used to define position rasterization. These variables represent the radial and transaxial offsets, or centroid positions, for each of the heads A and B, respectively. It will be noted that at least the tilting angle of the head is variable, although in the E.CAM gantry, such has not proven necessary for measurement and correction. During rasterization, the four variables $r_A$, $t_A$, $r_B$, $t_B$ are each stepped discretely through a chosen range, with all combinations of the parameters being tested.

Figure 7:
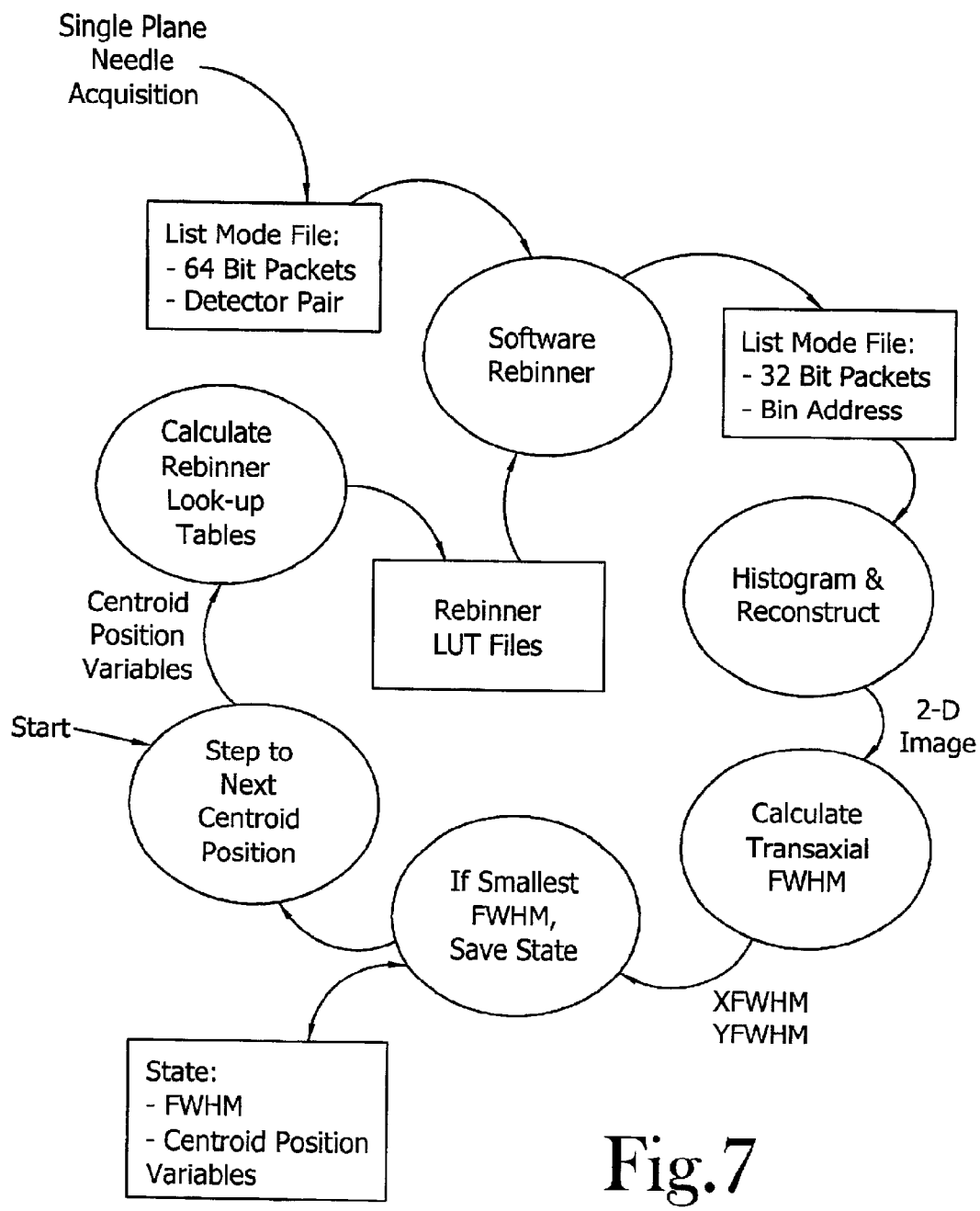
FIG. 7 is a schematic illustration of the process used to determine the optimal positions, and thus the centroid locations, of the detector banks.

The optimal positions, and thus the centroid locations, are found using the process depicted in FIG. 7. A 64-bit list mode file is collected once and read a multiple of times. The process is initiated by assuming a crystal position as the centroid for each of the heads A,B. A sequence for varying the assumed positions is also defined at the outset. For example, stepping through a 1 mm range in 0.1 mm steps, the steps in the sequence may be as follows. First, the indicated rebinning look up tables are made. Next, the list mode data is rebinned. The image is then histogrammed and reconstructed. Following this step, the image resolution is assessed. Next, the best resolution number and the associated trial position variables are recorded. These steps are then repeated on the next trial variable set. All FWHM resolution numbers are assessed from a conventional 2-D filtered back projection of the sinogram using a ramp filter with a 0.5 cutoff. In all applications, both image horizontal and vertical FWHM assessments are performed. Only the higher of the two FWHM is used for making decisions.

Initially, the four centroid locations are found using only LSO-LSO coincidence data. The sequence involves the rasterization of the four variables compensated not only for detector physics but also for simple mechanical variation in the mounting of the detectors. Once the centroid positions for the LSO crystals are known, a simpler problem remains for finding the NaI centroid locations. The NaI transaxial locations are assumed to be equivalent to the LSO case. Only the NaI radial locations remain to be determined. This determination requires a step-sequence with only one variable as opposed to four. Both head A and head B radial NaI offsets are assumed to vary equally, thus avoiding the need for two radial variables. Only LSO-NaI coincidence data is used for finding this fifth radial offset position. During rasterization, which is a step-sequence as described, the position variable is allowed to affect only the NaI end of each LOR. The LSO end of each LOR use the four LSO-only position parameters as determined and fixed earlier.

To this point, rasterization has been performed on data collected with the needle source positioned very close to the FOV center. Once these five position parameters (four for LSO crystals and one for NaI crystals) are determined, the final rebinning look-up table is defined. This look-up table is then applied for general use, including for LOR which do not serve the FOV center.

In one application of the present invention, needle activity ($^{68}$Ge/Ga) was contained within a 0.16 cm I.D. stainless steel tube and oriented parallel to the axis of the FOV. All data collected were in 64-bit detector-pair list-mode data format from a single 2-D plane (plane 80 of 167, segment 0, span 7). Coincidence time resolution was set up to 10 ns. Energy thresholds were set to 400 & 650 keV. All data was nearest-neighbor rebinned into a 256×256 sinogram with 0.2145 cm transaxial bin pitch by software which accurately emulates the rebinner card. Gamma centroid measurements to +/−0.01 cm were made by rastering assumed radial head positions and the corresponding rebinning maps for optimal back-projected image resolution. All FWHM resolution numbers were assessed from a conventional filtered back projection of the sinogram using a ramp filter with a 0.5 cutoff. In each case, both image horizontal and vertical FWHM assessments were performed. The tables below report the larger of those two resolution numbers. In Table 1 are the on-center transaxial FWHM spatial resolution results for LSO PET/SPECT in PET mode. In Table 2 are the 10 cm off-center results. In each of these tables, "ALL" means all LSO-LSO, LSO-NaI, Nai-LSO, and NaI-NaI coincidence events.

TABLE 1

PET Mode On-Center Transaxial FWHM Spatial Resolution

| Coincidence Type | FWHM (cm) | % Total Trues |
|---|---|---|
| LSO-LSO (only) | 0.39 | 60 |
| ALL | 0.42 | 100 |
| ALL (DOI disabled) | 0.52 | 100 |

TABLE 2

PET Mode Off-Center (10 cm) Transaxial FWHM Spatial Resolution

| Coincidence Type | FWHM (cm) | % Total Trues |
|---|---|---|
| LSO-LSO (only) | 0.57 | 60 |
| ALL | 0.59 | 100 |
| ALL (DCI disabled) | 0.70 | 100 |

Figure 8:
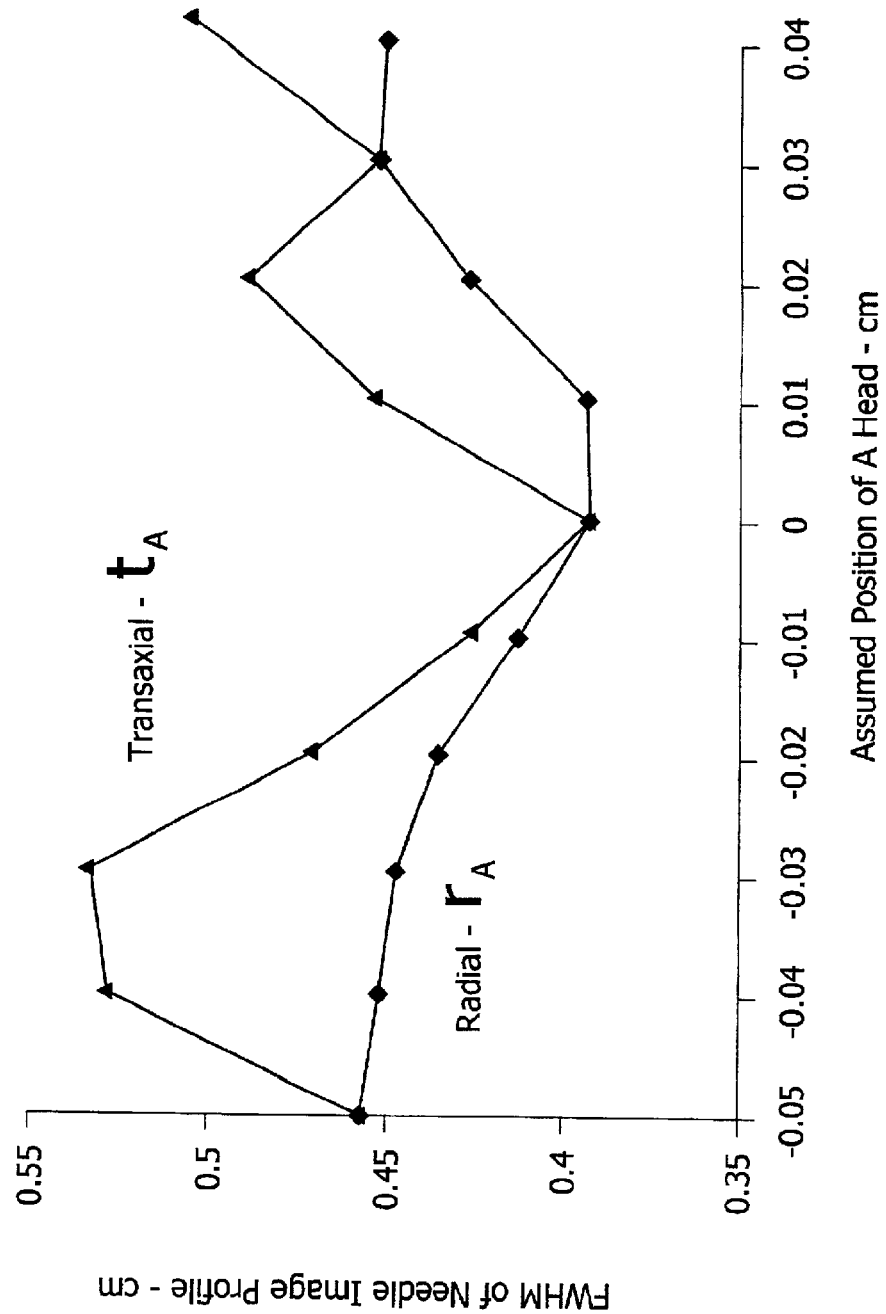
FIG. 8 illustrates a plot of found centroid locations as determined using the process depicted in FIG. 7.

FIG. 8 illustrates a plot of found centroid locations. The plot illustrates transaxial resolution versus transaxial and radial head position for LSO-LSO coincidences of a centered needle. Using only LSO-LSO coincidences, a few hundred trial positions were sequenced using software to implement the sequence of FIG. 7. Because of the difficulty in depicting a 4-dimensional space, FIG. 8 shows the impact on image resolution as 2 parameters of head A are sequenced optimally, one parameter at a time. As the assumed transaxial and radial position of head A varies through a 0.09 cm range in 0.01 cm steps, the impact on image resolution is shown. The upper, transaxial plot shows the resolution ranging from 0.53 cm to the optimal 0.39 cm as the assumed head A position is moved transaxially. The lower, radial plot shows the resolution ranging from 0.46 cm to the optimal 0.39 cm as the assumed head position is moved radially. As the assumed transaxial position of head A changes only by 0.03 cm, the resolution improves by over 20%, from 0.53 cm to 0.39 cm.

FIGS. 9A–9C display the sinograms and optimized images from the on-line center needle data collection. LSO-LSO coincidence data was used exclusively. FIG. 9A is a 256×256 sinogram resulting from the optimal placement of the gamma centroid locations. FIG. 9B is a 128×128 back-projection of the sinogram shown in FIG. 9A. A zoom of 10 was used in reconstruction along with a ramp filter with 0.5 cutoff. The profile FWHM is 0.39 cm. FIG. 9C is a back-projection of the sinogram shown in FIG. 9A, similar to the image of FIG. 9B, except with the intensity gray scale set to saturate above 10% to show background structure.

FIGS. 10A–C illustrate the sinograms and images from the off-center needle data collection, the offset being 10 cm. These images use the centroid locations determined by the data shown in FIGS. 9A–9C. As in FIGS. 9A–9C, LSO-LSO coincidence data was used exclusively. FIG. 10A is a 256×

256 sinogram resulting from the needle placement at 10 cm below FOV center. Optimal gamma centroid locations were determined by the on-center data used in the sinograms of FIGS. 9A–9C. FIG. 10B is a 128×128 back-projection of the sinogram shown in FIG. 10A. A zoom of 10 was used in reconstruction along with a ramp filter with 0.5 cutoff and a 10 cm offset. The profile FWHM is 0.57 cm. FIG. 10C is a back-projection of the sinogram shown in FIG. 10A, similar to the image of FIG. 10B, except with the intensity gray scale set to saturate above 10% to show background structure.

Figure 11:
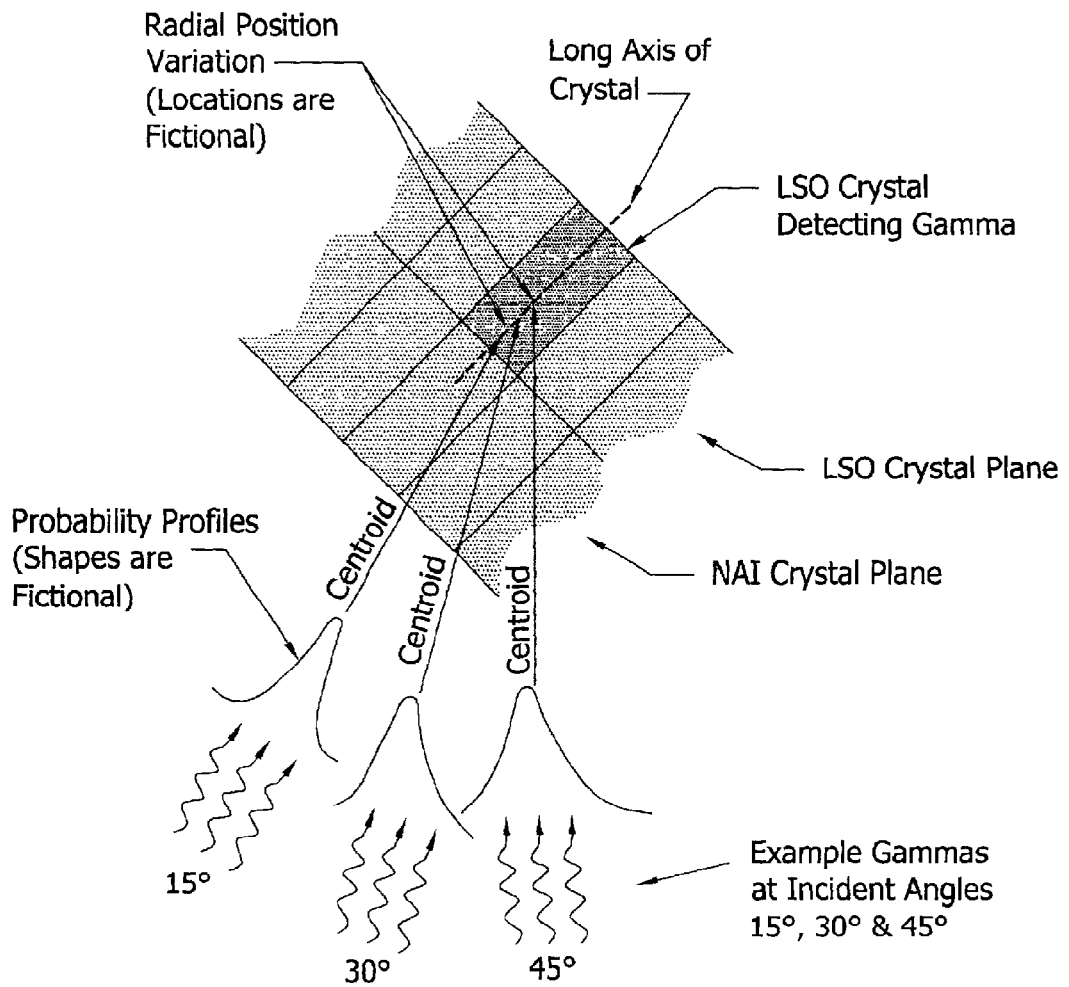
FIG. 11 illustrates various incident angles of gamma photons striking a detector array.

Image resolution is further improved by assessing the centroid locations as a function of gamma incident angles. FIG. 11 illustrates the incident angle parameter. In this illustration, gamma photons arrive at the detector array through a range of incident angles. Shown are angles of 15°, 30° and 45°. With each of these angles is shown a detection probability profile for the indicated crystal, each profile having a centroid. As each centroid intersects the crystal long axis at a different point, custom hardware applies such LOR position refinements in real time. As discussed above, a single centroid position is determined for each crystal in a planar array. In this concept extension for incident angle optimization, separate gamma interaction centroid locations are found for each incident angle range. Once the optimal locations are found, real-time application of the centroid location is performed in the rebinner. To this extent, list-mode data is grouped into incident angle subsets, after which rasterization is performed.

The LSO PET/SPECT device and method as described in the illustrated example has proven to achieve excellent 0.4 cm transaxial spatial resolution with effective on-line DOI rebinning capability at the center of the FOV and 0.6 cm transaxial spatial resolution with effective on-line DOI rebinning capability at 10 cm off center of the FOV.

From the foregoing description, it will be recognized by those skilled in the art that a method and apparatus for on-line DOI rebinning for LSO PET/SPECT to improve spatial resolution offering advantages over the prior art has been provided. Specifically, the present method and apparatus are useful in a hybrid PET/SPECT system running in PET-mode, and especially for such a system having a rotating dual-head tomograph using LSO/NaI scintillators and capable of depth-of-interaction measurement.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, we claim:

1. A method for improving spatial resolution using on-line depth-of-interaction (DOI) rebinning in a hybrid Positron Emission Tomography (PET)/Single Photon Emission Computed Tomography (SPECT) system running in PET-mode, the PET/SPECT system having a rotating dual-head tomograph using LSO/NaI scintillators and being capable of depth-of-interaction (DOI) measurement, the tomograph defining a field of view (FOV) within a patient gantry, said method comprising the steps of:
 (a) acquiring a PET coincidence data stream from a patient scan;
 (b) delivering the PET coincidence data stream to an on-line rebinner to derive a bin address output stream;
 (c) deriving a bin address output stream in said on-line rebinner from said PET coincidence data stream;
 (d) delivering the bin address output stream from the rebinner to a Fibre Channel PCI DMA receiver card for direct PCI DMA stream transfers;
 (e) histogramming the bin address output stream; and
 (f) storing said bin address output stream.

2. The method of claim 1 wherein said on-line rebinner is integrated within a rebinner circuitry which supports on-line real-time DOI line of response (LOR)-to-projection-space nearest-neighbor rebinning, and wherein DOI and gamma interaction centroid depth knowledge about LOR positioning is applied in real time.

3. The method of claim 1 wherein said step of deriving said bin address output stream includes performing a transaxial computation to determine at least a sinogram angle and a radial offset of a coincidence event between a first detector having coordinates $(x_A, y_A)$ of a first detector head and a second detector having coordinates $(x_B, y_B)$ of a second detector head, wherein said sinogram angle is determined by the equation:

$$sa = \tan^{-1}\left[\frac{y_b - y_a}{x_b - x_a}\right],$$

and where said radial offset is determined by the equation:

$$ro = \sqrt{(x_a^2 + y_a^2)} * \sin(\tan^{-1}(y_a/x_a) - sa).$$

4. The method of claim 1 further comprising the step of measuring a Gamma centroid location including the steps of:
 (1) rastering assumed transaxial and radial head positions and a corresponding rebinning map for optimal back-projected image resolution, said step rastering using variables $r_A, t_A, r_B, t_B$ to represent radial and transaxial offsets for each head of the dual-head tomograph; and
 (2) stepping the values for $r_A, t_A, r_B, t_B$ discretely through a chosen range, with all combinations of the variables being tested.

5. The method of claim 1 further comprising the step of finding an optimal position of each head of the dual-head tomograph including the steps of:
 (1) collecting a 64-bit list mode file;
 (2) assuming a crystal position as the centroid for each head; and
 (3) defining a sequence for varying the assumed crystal positions.

6. The method of claim 5 wherein said sequence for varying the assumed crystal positions includes the steps of:
 (i) making at least one rebinning look up table;
 (ii) rebinning list mode data;
 (iii) histogramming and reconstructing the image;
 (iv) assessing image resolution using Full Width Half Maximum (FWHM) resolution;
 (v) recording a best resolution number and an associated trial position variable; and
 (vi) repeating said steps of rebinning list mode data through said step of recording a best resolution number and an associated trial position variable on a subsequent trial variable set.

7. The method of claim 6, in said step of assessing image resolution, wherein all FWHM resolution numbers are assessed from a conventional 2-D filtered back projection of the sinogram using a ramp filter with a 0.5 cutoff.

8. The method of claim 6, in said step of assessing image resolution, wherein both image horizontal and vertical FWHM assessments are performed.

9. The method of claim 6 further comprising the step of defining a final rebinning look-up table to be applied for general use, including for LOR which do not serve the FOV center.

10. A method for improving spatial resolution using on-line depth-of-interaction (DOI) rebinning in a hybrid Positron Emission Tomography (PET)/Single Photon Emission Computed Tomography (SPECT) system running in PET-mode, the PET/SPECT system having a rotating dual-head tomograph using LSO/NaI scintillators and being capable of depth-of-interaction (DOI) measurement, the tomograph defining a field of view (FOV) within a patient gantry, said method comprising the step of:

finding multiple gamma interaction centroid locations which are unique for different line of response (LOR) incident angles.

* * * * *